US009504691B2

(12) United States Patent (10) Patent No.: US 9,504,691 B2
Boudreaux et al. (45) Date of Patent: Nov. 29, 2016

(54) FINAFLOXACIN SUSPENSION COMPOSITIONS

(71) Applicant: ALCON RESEARCH, LTD., Fort Worth, TX (US)

(72) Inventors: Brent G. Boudreaux, Irving, TX (US); Mark J. Bridle, Keller, TX (US); Bryan H. Huynh, Fort Worth, TX (US); Malay Ghosh, Fort Worth, TX (US); Masood A. Chowhan, Arlington, TX (US); Laman Alani, Fort Worth, TX (US); Bhagwati P. Kabra, Euless, TX (US)

(73) Assignee: Alcon Research, Ltd., Fort Worth, TX (US)

(*) Notice: Subject to any disclaimer, the term of this patent is extended or adjusted under 35 U.S.C. 154(b) by 0 days.

(21) Appl. No.: 14/086,651

(22) Filed: Nov. 21, 2013

(65) Prior Publication Data

US 2014/0162990 A1 Jun. 12, 2014

Related U.S. Application Data

(60) Provisional application No. 61/734,268, filed on Dec. 6, 2012.

(51) Int. Cl.
 *A61K 31/5383* (2006.01)
 *A61K 31/573* (2006.01)
 *A61K 47/02* (2006.01)
 *A61K 47/38* (2006.01)
 *A61K 9/00* (2006.01)
 *A61K 9/10* (2006.01)

(52) U.S. Cl.
 CPC ......... *A61K 31/5383* (2013.01); *A61K 9/0043* (2013.01); *A61K 9/0046* (2013.01); *A61K 9/0048* (2013.01); *A61K 9/10* (2013.01); *A61K 31/573* (2013.01); *A61K 47/02* (2013.01); *A61K 47/38* (2013.01)

(58) Field of Classification Search
 None
 See application file for complete search history.

(56) References Cited

U.S. PATENT DOCUMENTS

| | | | |
|---|---|---|---|
| 8,536,167 B2* | 9/2013 | Stroman et al. | 514/229.2 |
| 2002/0187193 A1 | 12/2002 | Roy et al. | |
| 2003/0069253 A1* | 4/2003 | Cagle et al. | 514/253.08 |

(Continued)

FOREIGN PATENT DOCUMENTS

| | | |
|---|---|---|
| WO | 97/10236 | 3/1997 |
| WO | 00/18386 | 4/2000 |

(Continued)

OTHER PUBLICATIONS

Dohar, Joseph E.: "Eardrops for otorrhea", Jan. 1, 2004 (Jan. 1, 2004), Advanced therapy of Otitis Media, pp. 246-253, XP009139207.

Goffin, Floyd B. et al: "pH as a factor in external otitis", New England Journal of Medicine, Massachusetts Medical Society, US, vol. 268, No. 6, Feb. 7, 1963 (Feb. 7, 1963), pp. 287-289, XP009139268.

(Continued)

*Primary Examiner* — Marcos Sznaidman
*Assistant Examiner* — Rayna B Rodriguez
(74) *Attorney, Agent, or Firm* — Mark Flanigan

(57) ABSTRACT

The present invention relates to methods for treating an ophthalmic, otic, or nasal infection comprising treating the infected tissue with a suspension composition comprising finafloxacin or a finafloxacin derivative. The present invention also relates to antimicrobial compositions comprising finafloxacin free base or a finafloxacin derivative. The compositions are suitable for the treatment of ophthalmic, otic, or nasal infections.

12 Claims, 2 Drawing Sheets

(56) References Cited

U.S. PATENT DOCUMENTS

2004/0072809 A1* 4/2004 Demopulos et al. ......... 514/171
2011/0003803 A1 1/2011 Stroman et al.

FOREIGN PATENT DOCUMENTS

| WO | 0200196 A2 | 1/2002 |
| WO | WO 2004/087043 A2 * | 10/2004 |
| WO | 2010/011942 | 1/2010 |
| WO | WO 2011/003091 A1 * | 1/2011 |
| WO | 2011/033091 | 3/2011 |

OTHER PUBLICATIONS

Higgins, Paul G. et al: "Activity of the investigational fluoroquinolone finafloxacin against ciprofloxacin-sensitive and -resistant acinetobacter baumannii isolates", Antimocrobial Agents and Chemotherapy, American Society for Microbiology, US, vol. 54, No. 4, Jan. 1, 2010 (Jan. 1, 2010), pp. 1613-1615, XP009139244.
Wohlert et al., "New fluoroquinolone finafloxacin HCl (FIN): route of synthesis, physicochemical characteristics and activity under neutral and acid conditions", IDSA, 2008, 46th Annual Meeting, F1-2036, published Dec. 31, 2008.

* cited by examiner

XRPD patterns of Finafloxacin free base, top to bottom:

1. Pattern C with weak A peaks
2. Disordered crystalline pattern C
3. Pattern B with weaker A peaks
4. Reference pattern B

FINAFLOXACIN SUSPENSION COMPOSITIONS

TECHNICAL FIELD OF THE INVENTION

The present invention generally relates to suspension compositions comprising a fluoroquinolone. The present invention specifically relates to suspension compositions comprising finafloxacin or a finafloxacin derivative.

BACKGROUND OF THE INVENTION

Quinolone antibiotics are known to have desirable broad-spectrum antimicrobial properties. For example, quinolone compounds for use in the treatment of ophthalmic, otic, and nasal conditions are disclosed in U.S. Pat. No. 6,716,830, the entire contents of which are incorporated by reference herein.

For use in pharmaceutical therapeutics, quinolone antibiotics must be formulated as stable, efficacious compositions. Unstable compositions can precipitate particulate matter when stored for a period of time, or can experience degradation of the active pharmaceutical ingredient or an excipient. Such compositions are unlikely to be approved by regulatory agencies due to safety concerns and other considerations.

Finafloxacin is a broad-spectrum fluoroquinolone that has been previously disclosed in U.S. patent application Ser. No. 12/829,973 for the treatment of ophthalmic, otic, and nasal infection. Finafloxacin antimicrobial activity peaks at pH ranges between 5 and 6. However, aqueous solutions of finafloxacin with this pH were found to have precipitates form in stability studies. Accordingly, new compositions of finafloxacin with better stability characteristics are needed.

BRIEF SUMMARY OF THE INVENTION

The present invention relates to suspension compositions comprising finafloxacin or a pharmaceutically acceptable salt, derivative, enantiomer, or hydrate thereof. Such finafloxacin compositions are for the treatment of microbial infection, including ophthalmic, otic, and nasal infections.

As noted above, finafloxacin has the greatest antimicrobial efficacy at low pH. However, solution compositions of finafloxacin suffered from low solubility and stability at the optimum pH, often producing undesired precipitates. The present invention provides stable, efficacious finafloxacin suspension compositions. Preferred finafloxacin suspensions have a soluble fraction of finafloxacin greater than 0.05% w/v and have a ratio of suspended to soluble finafloxacin between 18 to 1 and 1 to 1.

An embodiment of the present invention is a method for treating an infected tissue comprising treating the infected tissue with a topical suspension composition comprising finafloxacin. In a preferred embodiment, once a day dosing of the topical suspension is used to treat the infected tissue. Suspension formulations of the present invention are particularly useful in low frequency dosing regimens as the high soluble fraction of finafloxacin can provide immediate antimicrobial activity while the suspended fraction dissolves over time to provide extended duration of action.

Yet another embodiment of the present invention relates to suspension compositions comprising finafloxacin free base. A particularly preferred finafloxacin free base suspension composition comprises finafloxacin free base form A, which is stable at elevated temperatures used to heat sterilize such compositions. Preferred suspensions also comprise a solubilizer such as a divalent cation species to increase the soluble finafloxacin fraction in the composition.

The foregoing brief summary broadly describes the features and technical advantages of certain embodiments of the present invention. Additional features and technical advantages will be described in the detailed description of the invention that follows. Novel features which are believed to be characteristic of the invention will be better understood from the detailed description of the invention when considered in connection with any accompanying figures. However, figures provided herein are intended to help illustrate the invention or assist with developing an understanding of the invention, and are not intended to be definitions of the invention's scope.

BRIEF DESCRIPTION OF THE DRAWINGS

A more complete understanding of the present invention and the advantages thereof may be acquired by referring to the following description, taken in conjunction with the figures of the accompanying drawing in which like reference numbers indicate like features and wherein.

DETAILED DESCRIPTION OF THE INVENTION

The compositions of the invention are particularly directed toward treating mammalian and human subjects having or at risk of having a microbial tissue infection. Microbial tissue infections that may be treated or prevented in accord with the method of the present invention are referred to in J. P. Sanford et al., "The Sanford Guide to Antimicrobial Therapy 2007" 37$^{th}$ Edition (Antimicrobial Therapy, Inc.). Particular microbial tissue infections that may be treatable by embodiments of the present invention include those infections caused by bacteria, protozoa, fungi, yeast, spores, and parasites. The present invention is also particularly directed to antimicrobial suspension compositions for and methods of treating ophthalmic, otic, and nasal/sinus infections.

The suspension compositions of the present invention comprise finafloxacin or a pharmaceutically acceptable salt, derivative, enantiomer, or hydrate thereof. Finafloxacin (8-cyano-1-cyclopropyl-6-fluoro-7-[(4aS,7aS)-hexahydro-pyrrolo[3,4-b]-1,4-oxazin-6(2H)-yl]-1,4-dihydro-4-oxo-3-quinolinecarboxylic acid) has the following structure:

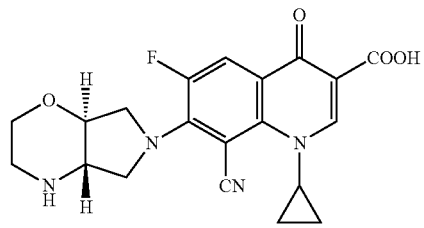 [SMILES: N#Cc1c(N2C[C@@H]3NCCO[C@H]3C2)c(F)cc2c(=O)c(C(=O)O)cn(C3CC3)c12]

Figure 1:
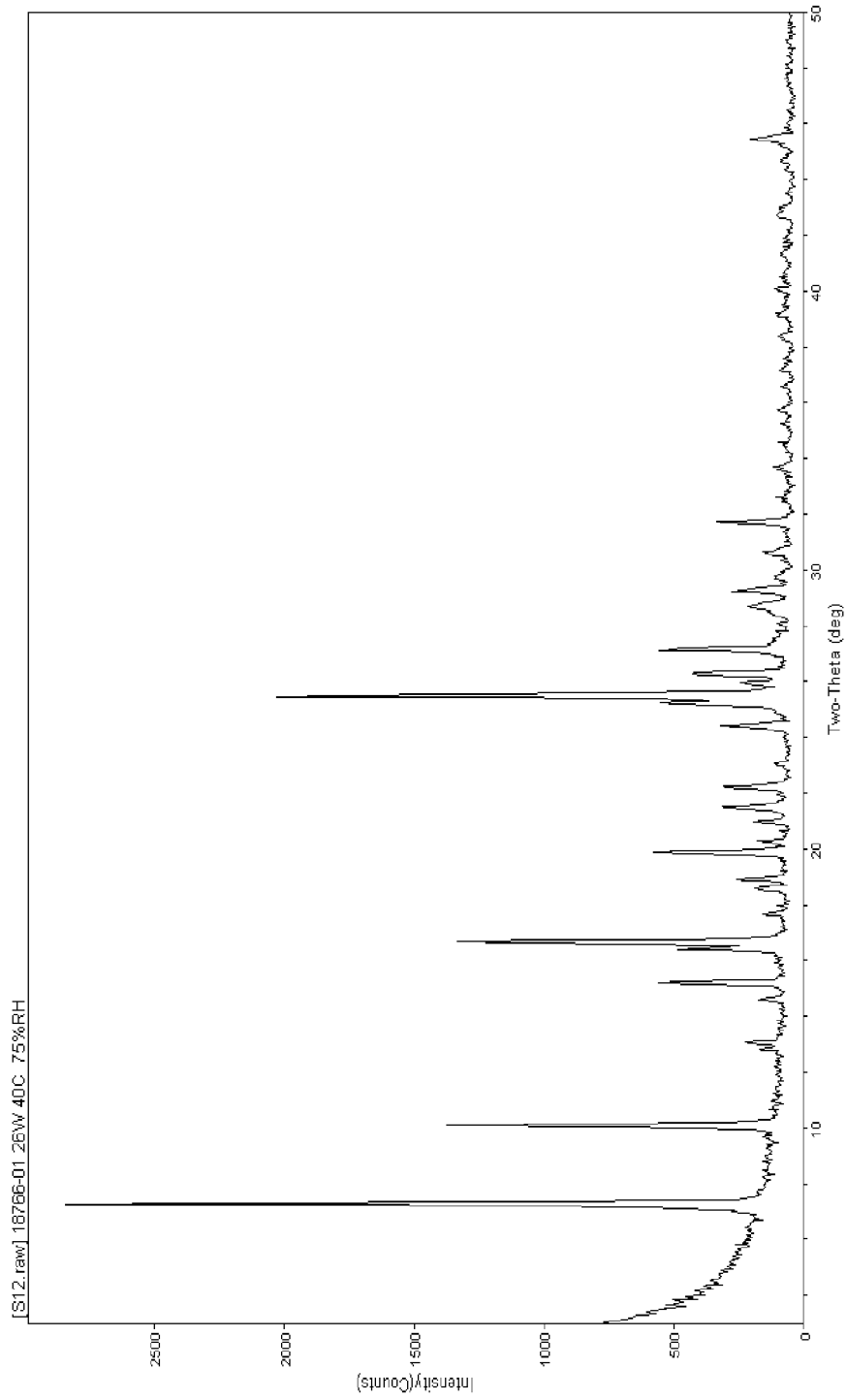
FIG. 1 illustrates the x-ray diffraction pattern of the form A crystalline form of finafloxacin free base.
Figure 2:
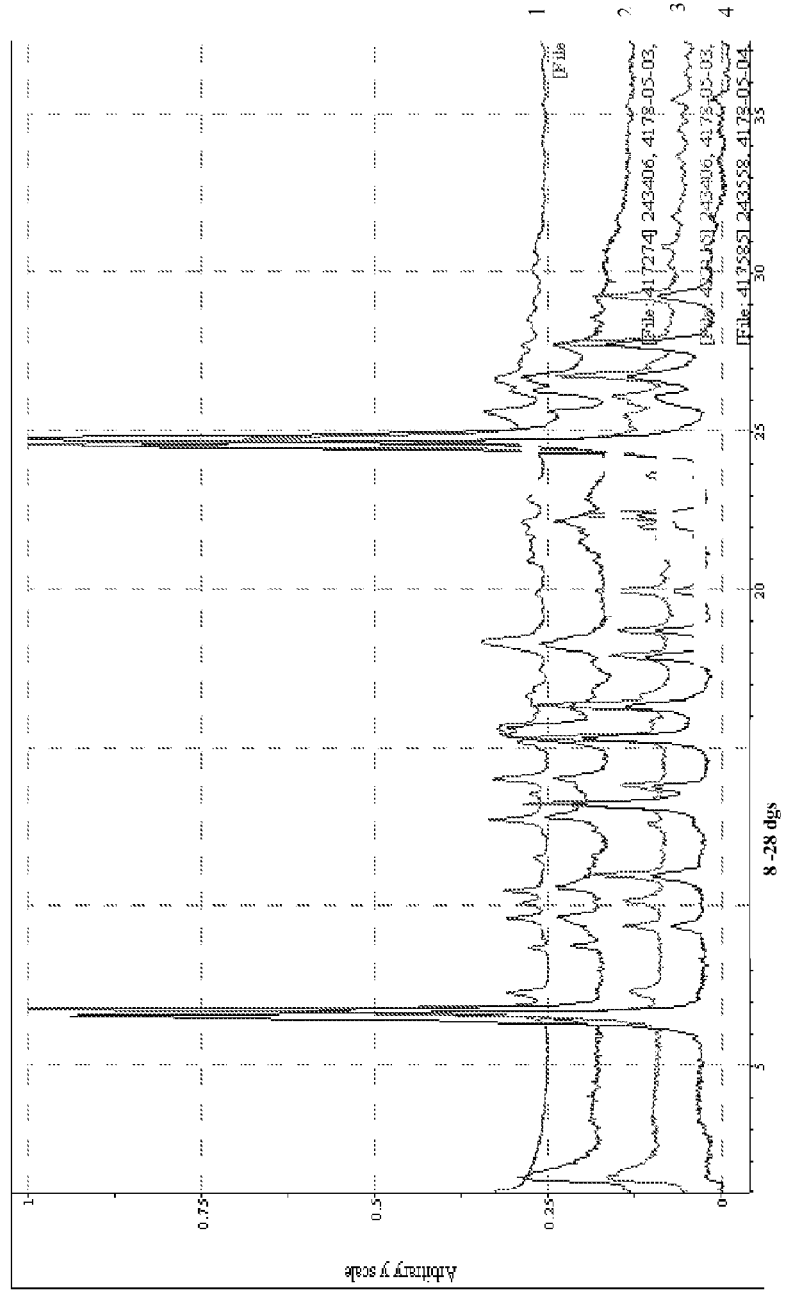
FIG. 2 illustrates overlay x-ray diffraction patterns of form B and form C of finafloxacin free base.

A preferred form of finafloxacin for use in embodiments of the present invention is finafloxacin free base. At least three polymorphs of the finafloxacin free base have been identified (forms A, B, and C). Substantially pure finafloxacin free base form A is utilized in preferred embodiments, as it was discovered to be the most stable at high temperatures such as those encountered during heat sterilization. The crystalline form of finafloxacin free base form A has an X-ray diffraction spectrum substantially the same as the X-ray powder diffraction spectrum shown in FIG. 1. The X-ray powder diffraction spectrums of form B and form C of finafloxacin free base are shown in FIG. 2.

As used herein, the term "substantially pure" with reference to a particular polymorphic form means that the polymorphic form includes less than 10%, preferably less than 5%, more preferably less than 3%, most preferably less than 1% by weight of any other physical forms of the compound.

As used herein, the term "essentially the same" with reference to X-ray diffraction peak positions means that the typical peak position and intensity variability are taken into account. For example, one skilled in the art will appreciate that the peak positions (2θ) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only.

Diasteromerically and enantiomerically pure finafloxacin is also preferred for use in embodiments of the present invention. As used herein, the term "finafloxacin" is intended to encompass finafloxacin and its pharmaceutically acceptable salts, derivatives, enantiomers, or hydrates. The phrase "pharmaceutically acceptable" is art-recognized and refers to compositions, polymers and other materials and/or dosage forms which are suitable for use in contact with the tissues of human beings and animals without excessive toxicity, irritation, allergic response, or other problem or complication, commensurate with a reasonable benefit/risk ratio as determined by one of ordinary skill in the art.

Finafloxacin and derivatives thereof can be synthesized according to the methods described in U.S. Pat. No. 6,133,260 to Matzke et al., the contents of which are herein incorporated by reference in their entirety. Finafloxacin free base form A is generated by treating finafloxacin hydrochloride with a hydroxide salt and then heating in water prior to drying. Finafloxacin form A may also be obtained in the solid state from finafloxacin free base form B with heat and/or vacuum drying. Furthermore, in the drug product compounding process, finafloxacin free base form A can be similarly be obtained from finafloxacin free base form B by heating in the aqueous phase.

Suspension compositions of the present invention generally comprise finafloxacin at a concentration of 0.001 w/v % or greater. In a preferred embodiment, a composition of the present invention comprises finafloxacin at a concentration of 0.15 to 2.0 w/v %. In a more preferred embodiment, a composition of the present invention comprises finafloxacin at a concentration of 0.20 to 1.0 w/v %, and in another preferred embodiment comprises finafloxacin at a concentration of 0.25 to 0.60 w/v %. The concentrations listed refer to the total quantity of finafloxacin by weight in the suspension composition and include finafloxacin dissolved in the solution fraction and the particulate finafloxacin in the suspension fraction of the composition.

The ratio of suspended finafloxacin to solubilized finafloxacin in the suspension composition may vary, but is typically between 18:1 and 1:1. In a preferred embodiment, the ratio is between 8:1 and 1:1. In a more preferred embodiment, the ratio is 4:1 to 2:1.

The soluble finafloxacin concentration of the suspensions may vary, but is typically greater than 0.05 w/v %. In a preferred embodiment, the soluble finafloxacin concentration is greater than 0.075 w/v %, and in a most preferred embodiment, the soluble finafloxacin concentration is greater than 0.1 w/v %. In certain preferred embodiments, a high soluble fraction is maintained in a stable suspension having a preferred pH of 5.6 to 6.5 and a most preferred pH of 5.8 to 6.2 and a concentration of solubilizer (such as magnesium chloride) of 0.02 to 0.1 w/v %. Suspensions with a pH outside this range often have undesirable polymorph changes or particulate growth as shown in Example 10 below. In a preferred embodiment of the present invention, finafloxacin suspensions are comprised substantially of finafloxacin free base form A (e.g., greater than 95% form A preferred; greater than 99% form A particularly preferred), and maintain this polymorphic form for a time period sufficient to meet stability standards (e.g., 12 months or greater in preferred embodiments, 12 months to 18 months in other embodiments, or 6 months to 18 months in yet other embodiments) at room temperature (15-25° C.).

It is generally desirable to maximize the soluble finafloxacin concentration, and solubilizers can be added to the suspension compositions to increase the amount of dissolved finafloxacin. While solubilizers known in the art can be used, divalent cations such as magnesium and calcium can be used in preferred embodiments. The concentration of such divalent cations can vary but is generally between 0.98 and 4.9 mM. In a preferred embodiment, the concentration of the divalent cation is between 2.0 and 3.9 mM, and in a most preferred embodiment the divalent cation concentration is between 2.5 and 3.4 mM. A particularly preferred solubilizer is magnesium salt such as magnesium chloride, magnesium acetate and magnesium oxide. A particularly preferred salt of magnesium is magnesium chloride. While the concentration of magnesium chloride may vary, a concentration of 0.02 to 0.10 w/v % is preferred, a concentration of 0.04 to 0.08 w/v % is more preferred, and a concentration of 0.05 to 0.07 is particularly preferred.

Suspension compositions of the present invention are prepared using a buffering system that maintains the composition at a pH of about 5.6 to 7. Preferred finafloxacin compositions have a pH of 5.6 to 6.5, and particularly preferred compositions have a pH of 5.8 to 6.2.

Milling agents to produce uniform finafloxacin particle sizes are also utilized in certain embodiments of the present invention. In a preferred embodiment, tyloxapol is used as a milling agent to produce finafloxacin mean volume particle sizes of less than 10 μm, and in a most preferred embodiment, less than 5 μm.

Suspending agents may also be used in certain embodiments to maintain a uniform suspension. Suspension uniformity can be measured by pouring a formulation into a 50 mL graduated cylinder at 25° C. and measuring the clear and unclear portions of the formulation over time as the formulation settles. Uniformity is the ratio (expressed as a percentage) of unclear formulation in the graduated cylinder. In preferred embodiments, such agents can maintain substantially uniform finafloxacin suspensions (i.e., with 95% or greater unclear suspended formulation) for a period greater than 4 hours, and in a most preferred embodiment greater than 8 hours. In a preferred embodiment, the suspending agent is hydroxyethylcellulose (HEC) at a concentration of 0.1 to 0.3 w/v %, and most preferably HEC at a concentration of 0.2 percent.

Finafloxacin suspensions of the present invention can be redispersed with shaking at 25° C. in less than 30 s in a preferred embodiment and less than 15 s in a most preferred embodiment.

Certain embodiments of the present invention are particularly useful for treating ophthalmic tissue infections. Examples of ophthalmic conditions that may be treated using compositions and methods of the present invention include conjunctivitis, keratitis, blepharitis, dacryocystitis, hordeolum and corneal ulcers. The methods and compositions of the invention may also be used prophylactically in various ophthalmic surgical procedures that create a risk of infection.

Otic and nasal/sinus tissue infections may also be treated by embodiments of the present invention. Examples of otic conditions that may be treated with compositions and methods of the present invention include acute otitis externa and otitis media (where the tympanic membrane has ruptured or tympanostomy tubes have been implanted). Examples of nasal/sinus conditions that may be treated with compositions and methods of the present invention include rhinitis, sinusitis, nasal carriage and situations where the nasal or sinus tissues are affected by surgery.

Embodiments of the present invention may also be used prophylactically to prevent infection of a tissue by an infectious agent. In such embodiments, a tissue at risk of infection is contacted with a composition of the present invention.

In particular embodiments, a composition of the present invention is administered once a day. However, the compositions of the present invention may also be formulated for administration at any frequency of administration, including once a week, once every 5 days, once every 3 days, once every 2 days, twice a day, three times a day, four times a day, five times a day, six times a day, eight times a day, every hour, or any greater frequency. Such dosing frequency is also maintained for a varying duration of time depending on the therapeutic regimen. The duration of a particular therapeutic regimen may vary from one-time dosing to a regimen that extends for weeks. One of ordinary skill in the art would be familiar with determining a therapeutic regimen for a specific indication that incorporates a pharmaceutically effective amount of finafloxacin or a composition thereof. The phrase "pharmaceutically effective amount" is an art-recognized term, and refers to an amount of an agent that, when incorporated into a pharmaceutical composition of the present invention, produces some desired effect at a reasonable benefit/risk ratio applicable to any medical treatment. The effective amount may vary depending on such factors as the disease or infectious agent being treated, the particular composition being administered, or the severity of the disease or infection agent.

In addition to finafloxacin, the compositions of the present invention optionally comprise one or more excipients. Excipients commonly used in pharmaceutical compositions include, but are not limited to, tonicity agents, preservatives, chelating agents, buffering agents, surfactants and antioxidants. Other excipients comprise solubilizing agents, stabilizing agents, comfort-enhancing agents, polymers, emollients, pH-adjusting agents and/or lubricants. Any of a variety of excipients may be used in compositions of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, xanthan gum, carrageenin, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of these products. In preferred embodiments, the concentration of the excipient(s) are, typically, from 0.01 to 100 times the concentration of finafloxacin and the excipient(s) are selected on the basis of their inertness towards finafloxacin.

Suitable tonicity-adjusting agents include, but are not limited to, mannitol, sodium chloride, glycerin, sorbitol and the like. Suitable buffering agents include, but are not limited to, phosphates, borates, acetates and the like. Suitable surfactants include, but are not limited to, ionic and nonionic surfactants, though nonionic surfactants are preferred, RLM 100, POE 20 cetylstearyl ethers such as Procol® CS20 and poloxamers such as Pluronic® F68. Suitable antioxidants include, but are not limited to, sulfites, ascorbates, butylated hydroxyanisole (BHA) and butylated hydroxytoluene (BHT).

The compositions set forth herein may comprise one or more preservatives. Examples of such preservatives include p-hydroxybenzoic acid ester, alkyl-mercury salts of thiosalicylic acid, such as thiomersal, phenylmercuric nitrate, phenylmercuric acetate, phenylmercuric borate, sodium perborate, sodium chlorite, parabens such as methylparaben or propylparaben, alcohols such as chlorobutanol, benzyl alcohol or phenyl ethanol, guanidine derivatives such as polyhexamethylene biguanide, sodium perborate, or sorbic acid. In certain embodiments, the composition may be self-preserved that no preservation agent is required. In preferred embodiments, a suspension composition is preserved to meet European Pharmacopoeia (Ph. Eur) standards with a benzalkonium chloride (BAC) concentration of 0.004 to 0.012 w/v %, with a most preferred BAC concentration of 0.005 w/v %.

For use in sinus applications, compositions may be used that comprise excipients suitable for aerosol formation using nebulizers or other such devices well known to those of skill in the art.

Some compositions of the present invention are ophthalmically suitable for application to a subject's eyes. In preferred aspects, compositions that include finafloxacin will be formulated for topical application to the eye in aqueous suspension in the form of drops. The term "aqueous" typically denotes an aqueous composition wherein the excipient is >50%, more preferably >75% and in particular >90% by weight water. These drops may be delivered from a single dose ampoule which may preferably be sterile and thus render bacteriostatic components of the composition unnecessary. Alternatively, the drops may be delivered from a multi-dose bottle which may preferably comprise a device which extracts any preservative from the composition as it is delivered, such devices being known in the art.

In other aspects, components of the invention may be delivered to the eye as a concentrated gel or a similar vehicle, or as dissolvable inserts that are placed beneath the eyelids. In yet other aspects, components of the invention may be delivered to the eye as ointment, water-in-oil and oil-in-water emulsions.

For topical compositions to the eye, the compositions are preferably isotonic, or slightly hypotonic in order to combat any hypertonicity of tears caused by evaporation and/or disease. This may require a tonicity agent to bring the osmolality of the composition to a level at or near 210-420 milliosmoles per kilogram (mOsm/kg). The compositions of the present invention generally have an osmolality in the range of 220-420 mOsm/kg, and preferably have an osmolality in the range of 260-330 mOsm/kg.

In certain embodiments, finafloxacin is formulated in a composition that comprises one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; and carbomers, such as carbomer 934P, carbomer 941, carbomer 940 and carbomer 974P. Certain compositions of the present invention may be used with contact lenses or other ophthalmic products.

In some embodiments, the compositions set forth herein have a viscosity of 0.5-100 cps, preferably 0.5-50 cps, and most preferably 1-20 cps. This relatively low viscosity insures that the product is comfortable, does not cause blurring, and is easily processed during manufacturing, transfer and filling operations.

In the methods set forth herein, administration to a subject of a pharmaceutically effective amount of a composition that includes finafloxacin may be by any method known to those of ordinary skill in the art. For example, the composition may be administered locally, topically, intradermally, intralesionally, intranasally, subcutaneously, orally, by inhalation, by injection, by localized perfusion bathing target cells directly, via a catheter, or via lavage.

In particular embodiments, the composition is administered topically to an ocular surface. Regarding ophthalmic administration, it is contemplated that all local routes to the eye may be used, including topical, subconjunctival, periocular, retrobulbar, subtenon, intraocular, subretinal, posterior juxtascleral, and suprachoroidal administration.

The compositions of the present invention may also comprise an anti-inflammatory agent. The compositions of the present invention may also contain one or more anti-inflammatory agents. The anti-inflammatory agents utilized in the present invention are broadly classified as steroidal or non-steroidal. The preferred steroidal anti-inflammatory agents are glucocorticoids. Glucocorticoids for ophthalmic, otic, or nasal use include dexamethasone, loteprednol, rimexolone, prednisolone, fluorometholone, hydrocortisone, mometasone, fluticasone, beclomethasone, flunisolide, triamcinolone and budesonide.

Non-steroidal anti-inflammatory agents include, but are not limited to, prostaglandin H synthetase inhibitors (Cox I or Cox II), also referred to as cyclooxygenase type I and type II inhibitors, such as diclofenac, flurbiprofen, ketorolac, suprofen, nepafenac, amfenac, indomethacin, naproxen, ibuprofen, bromfenac, ketoprofen, meclofenamate, piroxicam, sulindac, mefanamic acid, diflusinal, oxaprozin, tolmetin, fenoprofen, benoxaprofen, nabumetome, etodolac, phenylbutazone, aspirin, oxyphenbutazone, NCX-4016, HCT-1026, NCX-284, NCX-456, tenoxicam and carprofen; cyclooxygenase type II selective inhibitors, such as NS-398, vioxx, celecoxib, P54, etodolac, L-804600 and S-33516; PAF antagonists, such as SR-27417, A-137491, ABT-299, apafant, bepafant, minopafant, E-6123, BN-50727, nupafant and modipafant; PDE IV inhibitors, such as ariflo, torbafylline, rolipram, filaminast, piclamilast, cipamfylline, CG-1088, V-11294A, CT-2820, PD-168787, CP-293121, DWP-205297, CP-220629, SH-636, BAY-19-8004, and roflumilast; inhibitors of cytokine production, such as inhibitors of the NF.kappa.B transcription factor; or other anti-inflammatory agents known to those skilled in the art.

The concentrations of the anti-inflammatory agents contained in the compositions of the present invention will vary based on the agent or agents selected and the type of inflammation being treated. The concentrations will be sufficient to reduce inflammation in the targeted ophthalmic, otic or nasal tissues following topical application of the compositions to those tissues. Such an amount is referred to herein as "an anti-inflammatory effective amount". The compositions of the present invention will typically contain one or more anti-inflammatory agents in an amount of from about 0.01 to about 2.0 w/v %, preferably from 0.05 to 1.0 w/v %, and most preferably 0.05 to 0.2 w/v %. In a particularly preferred embodiment, the anti-inflammatory compound is dexamethasone at a concentration of 0.1 w/v %.

Various otic administration techniques are also contemplated. In particular embodiments, the composition may be delivered directly to the ear canal (for example: topical otic drops or ointments; slow release devices in the ear or implanted adjacent to the ear). Local administration routes include otic intramuscular, intratympanic cavity and intracochlear injection routes for the compositions. It is further contemplated that certain compositions of the invention may be formulated in intraotic inserts or implant devices. For instance, delivery of the compositions can be accomplished by endoscopic assisted (including laser-assisted endoscopy to make the incision into the tympanic membrane) injection into the tympanic cavity as set forth, for example, in Tsue et al., Amer. J. Otolaryngology, Vol. 16(3):158-164, 1995; Silverstein et al., Ear Nose Throat, Vol. 76:674-678, 1997; Silverstein et al., Otolaryngol Head Neck Surg, Vol. 120: 649-655, 1999. Local administration can also be achieved by injection through the tympanic membrane using a fine (EMG recording) needle, through use of an indwelling catheter placed through a myringotomy incision, and injection or infusion through the Eustachian tube by means of a small tubal catheter. Furthermore, the compositions can be administered to the inner ear by placement of gelfoam or similar absorbent and adherent product soaked with the compositions against the window membrane of the middle/inner ear or adjacent structure with due discretion and caution by a skilled clinician. Various other devices can be used to deliver the compositions to the affected ear compartment; for example, via catheter or as exemplified in U.S. Pat. No. 5,476,446 which provides a multi-functional apparatus specifically designed for use in treating and/or diagnosing the inner ear of the human subject. Also see U.S. Pat. No. 6,653,279 for other devices for this purpose.

The compositions of the present invention may be prepared by conventional methods of preparing aqueous pharmaceutical suspension compositions, including sizing the drug using known sizing techniques, such as ball-milling. For example, a slurry containing finafloxacin, a milling agent such as tyloxopol and milling beads is tumbled for a time sufficient to obtain drug of desired particle sizes. The sizing beads are then separated from the slurry and the slurry is added to the remaining aqueous ingredients. Preferably, however, the compositions of the present invention are made in a specific manner. According to the preferred method, finafloxacin is first added to a mixture of 1% tyloxopol in purified water with beads. The mixture is heated in an autoclave to sterilize the mixture (and to ensure conversion of the finafloxacin to the polymorph form A). The slurry is milled in aseptic conditions to preferably produce finafloxacin particles smaller than 10 μm mean volume. Following removal of the milling beads, the finafloxacin slurry is mixed with the remainder of the suspension components and pH adjusted.

Administration of the compositions described herein for the treatment of nasal infection can be via a number of methods known to those of skill in the art. For example, such compositions can be administered in droplet form or by aerosol formation.

EXAMPLES

Examples 1-7 below were prepared according to embodiments of the present invention.

Example 1

| Ingredient | % w/v |
| --- | --- |
| Finafloxacin | 0.1 to 1.0 |
| Tyloxapol | 0.01 |
| Hydroxyethylcellulose | 0.2 |

-continued

| Ingredient | % w/v |
|---|---|
| Sodium chloride | 0.86 |
| Magnesium chloride | 0.06 |
| Benzalkonium chloride | 0.005 |
| Sodium hydroxide | Adjust pH to 6 |
| Purified Water | q.s. 100% |

Example 2

| Ingredient | % w/v |
|---|---|
| Finafloxacin | 0.1 to 1.0 |
| Lactic Acid | 0.18 |
| Glycerin | 2.4 |
| Boric Acid | 0.3 |
| Tromethamine | Adjust pH to 6 |
| Purified Water | q.s. 100% |

Example 3

| Ingredient | % w/v |
|---|---|
| Finafloxacin Free Base | 0.3 |
| Tyloxapol | 0.01 |
| Hydroxyethylcellulose | 0.2 |
| Sodium chloride | 0.86 |
| Magnesium chloride | 0.12 |
| Benzalkonium chloride | 0.005 |
| Sodium hydroxide | Adjust pH to 5.8 |
| Purified Water | q.s. 100% |

Example 4

| Ingredient | % w/v |
|---|---|
| Finafloxacin Free Base | 0.3 |
| Tyloxapol | 0.01 |
| Hydroxyethylcellulose | 0.2 |
| Sodium chloride | 0.86 |
| Benzalkonium chloride | 0.005 |
| Sodium hydroxide | Adjust pH to 6.0 |
| Purified Water | q.s. 100% |

Example 5

| Ingredient | % w/v |
|---|---|
| Finafloxacin | 0.3 |
| Tyloxapol | 0.01 |
| Hydroxyethylcellulose | 0.2 |
| Sodium chloride | 0.86 |
| Magnesium chloride | 0.06 |
| Benzalkonium chloride | 0.005 |
| Sodium hydroxide | Adjust pH to 6 |
| Purified Water | q.s. 100% |

Example 6

| Ingredient | % w/v |
|---|---|
| Finafloxacin | 0.3 |
| Dexamethasone | 0.1 |
| Tyloxapol | 0.05 |
| Hydroxyethylcellulose | 0.2 |
| Sodium chloride | 0.86 |
| Magnesium chloride | 0.06 |
| Benzalkonium chloride | 0.005 |
| Sodium hydroxide | Adjust pH to 6 |
| Purified Water | q.s. 100% |

Example 7

| Ingredient | % w/v |
|---|---|
| Finafloxacin | 0.3 |
| Dexamethasone | 0.1 |
| Tyloxapol | 0.05 |
| Carboxymethylcellulose | 0.5 |
| Sodium chloride | 0.86 |
| Magnesium chloride | 0.06 |
| Benzalkonium chloride | 0.005 |
| Sodium hydroxide | Adjust pH to 6 |
| Purified Water | q.s. 100% |

Example 8

In Vitro Antimicrobial Efficacy Studies

A finafloxacin solution composition at pH 5.8 and 7.3 was compared to ciprofloxacin and ofloxacin compositions using standard in vitro antimicrobial susceptibility tests (M07-08 Methods for Dilution Antimicrobial Susceptibility Tests for Bacteria that Grow Aerobically; Approved Standard-Eighth Edition (January 2009, Clinical and Laboratory Standards Institute), herein incorporated by reference). Minimum inhibitory concentrations ($MIC_{50}$) were determined using organisms commonly found in otic and ophthalmic infections. The $MIC_{50}$ was the lowest concentration of antibiotic that prevented growth of the test organism, as determined visually by a lack of turbidity.

The results of the experiment are presented below in TABLES 1-5. At acidic pH, finafloxacin generally had greater activity against both Gram-positive and Gram-negative organisms than the fluoroquinolones ciprofloxacin and ofloxacin, both of which are used for the treatment of otic infections. Higher activity under acidic conditions is important for an otic formulation since a low pH formulation is preferred to slow bacterial and fungal growth, as well as the fact the pH environment of the external ear canal is ~pH 6.

TABLE 1

Antimicrobial Profiles of Finafloxacin and Comparator Fluoroquinolones against Ciprofloxacin-Resistant *S. aureus*

| | pH 5.8 | | | pH 7.3 | | |
|---|---|---|---|---|---|---|
| | Fina. | Ciprofloxacin | Ofloxacin | Fina. | Ciprofloxacin | Ofloxacin |
| Isolates | 12 | 12 | 12 | 12 | 12 | 12 |
| MIC90 | 8 | >256 | >512 | 16 | 128 | 256 |
| MIC50 | 4 | 128 | 64 | 16 | 128 | 32 |
| Range | 0.5-8 | 16->256 | 16->512 | 2-16 | 4-128 | 2-256 |

TABLE 2

Antimicrobial Profiles of Finafloxacin and Comparator
Fluoroquinolones against Ciprofloxacin-Susceptible S. aureus

|  | pH 5.8 | | | pH 7.3 | | |
|---|---|---|---|---|---|---|
|  | Fina. | Ciprofloxacin | Ofloxacin | Fina. | Ciprofloxacin | Ofloxacin |
| Isolates | 8 | 8 | 8 | 8 | 8 | 8 |
| MIC90 | N/A | N/A | N/A | N/A | N/A | N/A |
| MIC50 | 0.016 | 1 | 1 | 0.125 | 0.25 | 0.25 |
| Range | 0.008-0.125 | 0.5-0.4 | 0.5-64 | 0.016-0.25 | 0.125-1 | 0.125-0.5 |

TABLE 3

Antimicrobial Profiles of Finafloxacin and Comparator
Fluoroquinolones against Ciprofloxacin-Resistant P. aeruginosa

|  | pH 5.8 | | | pH 7.3 | | |
|---|---|---|---|---|---|---|
|  | Fina. | Ciprofloxacin | Ofloxacin | Fina. | Ciprofloxacin | Ofloxacin |
| Isolates | 11 | 11 | 11 | 11 | 11 | 11 |
| MIC90 | 512 | >512 | >512 | >512 | 512 | >512 |
| MIC50 | 16 | 64 | 256 | 512 | 16 | 64 |
| Range | 2-512 | 8->512 | 64->512 | 8->512 | 4-512 | 8->512 |

TABLE 4

Antimicrobial Profiles of Finafloxacin and Comparator
Fluoroquinolones against Ciprofloxacin-Susceptible P. aeruginosa

|  | pH 5.8 | | | pH 7.3 | | |
|---|---|---|---|---|---|---|
|  | Fina. | Ciprofloxacin | Ofloxacin | Fina. | Ciprofloxacin | Ofloxacin |
| Isolates | 14 | 14 | 14 | 14 | 14 | 14 |
| MIC90 | 4 | 8 | 32 | 16 | 2 | 4 |
| MIC50 | 1 | 1 | 4 | 4 | 0.5 | 2 |
| Range | 0.25-4 | 0.125-8 | 1-32 | 2-16 | 0.063-2 | 1-4 |

TABLE 5

Antimicrobial Profiles of Finafloxacin and Comparator
Fluoroquinolones against E. coli

|  | pH 5.8 | | | pH 7.3 | | |
|---|---|---|---|---|---|---|
|  | Fina. | Ciprofloxacin | Ofloxacin | Fina. | Ciprofloxacin | Ofloxacin |
| Isolates | 10 | 10 | 10 | 10 | 10 | 10 |
| MIC90 | 8 | >1024 | 512 | 64 | 128 | 16 |
| MIC50 | 4 | 256 | 512 | 32 | 16 | 16 |
| Range | 0.0078-8 | 0.063-0->1024 | 0.25-512 | 0.008-64 | ≤0.008-128 | 0.016-16 |

Example 9

In Vivo Acute Otitis Externa (AOE) Model

Finafloxacin test compositions (0.045 to 0.3% total finafloxacin) were evaluated in a guinea pig model of acute otitis externa (AOE) using *Pseudomonas aeruginosa*. Guinea pig ears were slightly abraded and 200 µl of bacterial culture ($10^8$ CFU) of *P. aeruginosa* were instilled into each ear. Ears were lavaged with saline and plated onto *Pseudomonas* isolation media. TABLE 6 summarizes the results of these studies. Generally, a soluble fraction of 0.05 w/v % finafloxacin was required to achieve sterilization of all ears. Compositions 9, 17, and 18 had a soluble fraction greater than 0.05 w/v %, but had a lower total concentration of finafloxacin (0.075, 0.075, and 0.1 w/v %, respectively).

TABLE 6

In vivo Efficacy Summary

| Composition | Ears Sterilized | Soluble Finafloxacin (w/v %) | Total Finafloxacin as free base (w/v %) |
|---|---|---|---|
| 1 | 4/4 | 0.059 | 0.3 |
| 2 | 2/4 | 0.044 | 0.3 |
| 3 | 2/4 | 0.047 | 0.3 |
| 4 | 2/4 | 0.044 | 0.3 |
| 5 | 4/4 | 0.055 | 0.3 |
| 6 | 4/4 | 0.093 | 0.3 |
| 7 | 4/4 | 0.147 | 0.3 |
| 8 | 0/4 | 0.045 | 0.045 |
| 9 | 2/4 | 0.075 | 0.075 |
| 10 | 4/4 | 0.15 | 0.015 |
| 11 | 4/4 | 0.035 | 0.3 |
| 12 | 4/4 | 0.088 | 0.3 |
| 13 | 4/4 | 0.156 | 0.3 |
| 14 | 4/4 | 0.034 | 0.3 |
| 15 | 4/4 | 0.089 | 0.3 |
| 16 | 4/4 | 0.157 | 0.3 |
| 17 | 0/4 | 0.075 | 0.075 |
| 18 | 2/4 | 0.10 | 0.1 |

TABLE 6-continued

In vivo Efficacy Summary

| Composition | Ears Sterilized | Soluble Finafloxacin (w/v %) | Total Finafloxacin as free base (w/v %) |
|---|---|---|---|
| 19 | 4/4 | 0.15 | 0.15 |
| 20 | 4/4 | 0.12 | 0.3 |
| 21 | 4/4 | 0.03 | 0.3 |
| 22 | 4/4 | 0.14 | 0.3 |
| 23 | 4/4 | 0.15 | 0.3 |

TABLE 6-continued

In vivo Efficacy Summary

| Composition | Ears Sterilized | Soluble Finafloxacin (w/v %) | Total Finafloxacin as free base (w/v %) |
|---|---|---|---|
| 24 | 4/4 | 0.075 | 0.15 |
| 25 | 4/4 | 0.11 | 0.15 |

Example 10

Stability Studies

Exploratory stability studies were conducted to physical and chemical stability characteristics of formulations of the present invention. The formulations studied are listed in Table 7 below.

| Ingredient | 1 (w/v %) | 2 (w/v %) | 3 (w/v %) |
|---|---|---|---|
| Finafloxacin | 0.3 | 0.3 | 0.3 |
| Tyloxapol | 0.01 | 0.02 | 0.01 |
| Magnesium chloride | 0.12 | 0.12 | 0.08 |
| Hydroxyethyl cellulose | 0.2 | 0.2 | 0.2 |
| Sodium chloride | 0.86 | 0.86 | 0.86 |
| Benzalkonium chloride | 0.005 | 0.005 | 0.005 |
| Sodium chloride and/or hydrochloric acid | pH to 5.5 | pH to 6.0 | pH to 6.2 |
| Purified water | QS 100% | QS 100% | QS 100% |

Formulation 1, with a pH of 5.5, was determined to not meet stability requirements due to the formation of needle-like particles of finafloxacin hydrochloride salt after 2 weeks. However, formulations 2 and 3 with pH of 6.0 and 6.2, respectively, did not exhibit finafloxacin hydrochloride particulate formation during the study. Other formulations of the present invention were tested (e.g., Example 1 above), and did not exhibit the finafloxacin hydrochloride particulate formation found at lower pH.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

What is claimed is:

1. A topical suspension composition comprising finafloxacin, a solubilizer, and a suspending agent, and wherein said finafloxacin is finafloxacin free base form A, said solubilizer is magnesium salt at a concentration of 0.98 to 4.9 mM, and said suspending agent is hydroxyethylcellulose at a concentration of 0.1 to 0.3 w/v %, and wherein said composition maintains substantial uniformity for greater than 8 hours at 25° C., and wherein said composition has a pH of 5.8 to 6.2 and said concentration of finafloxacin is 0.15 to 2.0 w/v %.

2. A composition according to claim 1, said composition having a ratio of suspended to solubilized finafloxacin between 18:1 and 1:1.

3. A composition according to claim 1, wherein said solubilizer is magnesium chloride at a concentration of 0.05 to 0.07 w/v %.

4. A composition according to claim 1, further comprising an anti-inflammatory agent.

5. A composition according to claim 4, wherein said anti-inflammatory agent is dexamethasone.

6. A composition according to claim 5, wherein said composition comprises dexamethasone at a concentration of 0.05 to 1.0 w/v %.

7. A method for treating an ophthalmic, otic, or nasal infection comprising: treating the infection with a pharmaceutically effective amount of a composition according to claim 1.

8. A method according to claim 7 wherein said infection is acute otitis externa or acute otitis media with tympanostomy tubes.

9. A method for preparing a finafloxacin suspension of claim 1 comprising: producing a finafloxacin slurry by adding finafloxacin free base, a milling agent, and milling beads together with water to form an aqueous slurry; and heating the slurry to form finafloxacin free base form A.

10. A method for preparing a finafloxacin suspension comprising:
producing a finafloxacin slurry by adding finafloxacin free base, a milling agent, and milling beads together with water to form an aqueous slurry; and
heating the slurry to form finafloxacin free base form A.

11. A method according to claim 10 wherein said finafloxacin slurry further comprises one or more anti-inflammatory agents.

12. A method according to claim 11 wherein said finafloxacin slurry further comprises dexamethasone.

* * * * *